United States Patent
Martin et al.

(10) Patent No.: US 10,449,012 B2
(45) Date of Patent: Oct. 22, 2019

(54) TRANSPORTATION OF MEDICAL INSTRUMENTS

(71) Applicant: TRISTEL PLC, Newmarket (GB)

(72) Inventors: Benjamin Alexander Martin, Newmarket (GB); Julija Shabanova, Newmarket (GB); Esther Jansen, Newmarket (GB)

(73) Assignee: TRISTEL PLC, Newmarket Cambridgeshire (GB)

( * ) Notice: Subject to any disclaimer, the term of this patent is extended or adjusted under 35 U.S.C. 154(b) by 0 days.

(21) Appl. No.: 15/756,733

(22) PCT Filed: Aug. 25, 2016

(86) PCT No.: PCT/GB2016/052652
§ 371 (c)(1),
(2) Date: Mar. 1, 2018

(87) PCT Pub. No.: WO2017/037431
PCT Pub. Date: Mar. 9, 2017

(65) Prior Publication Data
US 2018/0250091 A1 Sep. 6, 2018

(30) Foreign Application Priority Data

Sep. 4, 2015 (GB) .................................. 1515705.0
Apr. 21, 2016 (GB) .................................. 1606930.4

(51) Int. Cl.
*A61B 50/31* (2016.01)
*B65D 33/34* (2006.01)
(Continued)

(52) U.S. Cl.
CPC .............. *A61B 50/31* (2016.02); *A61B 50/30* (2016.02); *A61B 50/33* (2016.02); *A61B 50/36* (2016.02);
(Continued)

(58) Field of Classification Search
USPC ..... 206/363, 370, 807, 459.1, 459.5; 40/638
See application file for complete search history.

(56) References Cited

U.S. PATENT DOCUMENTS 2,153,310 A * 4/1939 Newman .................... G09F 3/02
206/820
3,854,581 A * 12/1974 Jones, Jr. .................... C09J 7/26
206/460
(Continued)

FOREIGN PATENT DOCUMENTS

DE 202007001713 U1 7/2007
EP 0515086 A1 11/1992
(Continued)

OTHER PUBLICATIONS

Non Transfer—Void Security Sticker; www.stickertapes.com/Non-Transfer-Warranty-Void-Security-Sticker-1.

*Primary Examiner* — Jacob K Ackun
(74) *Attorney, Agent, or Firm* — Hayes Soloway PC (57) ABSTRACT

A device for the transportation and temporary storage of a medical instrument including
an instrument bag material substantially impermeable to bodily fluids, the bag having a bag opening.
A label has a first portion adhered to an external surface of the bag adjacent to the bag opening and has a second portion disposed beyond the bag opening and which has a lower surface at least part of which is adhesive.
The first portion of the label includes a pocket for receiving a sachet or data carrier.
The second portion of the label includes a tamper-evident portion which exhibits a first visual appearance when first adhered to a surface of the bag, and which exhibits a second visual appearance after it has been adhered to and then
(Continued)

removed from a surface of the bag, and subsequently adhered to the same surface of the bag.

15 Claims, 11 Drawing Sheets (51) Int. Cl.
| | |
|---|---|
| *A61B 50/30* | (2016.01) |
| *A61B 50/36* | (2016.01) |
| *A61B 90/90* | (2016.01) |
| *A61B 50/33* | (2016.01) |
| *G09F 3/00* | (2006.01) |
| *A61B 90/00* | (2016.01) |
| *A61B 90/94* | (2016.01) |
| *A61B 90/98* | (2016.01) |
| *A61B 90/92* | (2016.01) |

(52) U.S. Cl.
CPC .............. *A61B 90/90* (2016.02); *B65D 33/34* (2013.01); *A61B 90/92* (2016.02); *A61B 90/94* (2016.02); *A61B 90/98* (2016.02); *A61B 2050/3015* (2016.02); *A61B 2050/314* (2016.02); *A61B 2090/037* (2016.02); *G09F 3/0292* (2013.01)

(56) References Cited

U.S. PATENT DOCUMENTS

| | | | | |
|---|---|---|---|---|
| 4,998,666 A * | 3/1991 | Ewan | ...................... | B65D 33/34 206/459.1 |
| 5,103,979 A * | 4/1992 | Hustad | ................... | B65D 33/34 206/459.1 |
| 5,225,162 A * | 7/1993 | Scoville | .................... | A61L 2/26 206/439 |
| 5,366,087 A * | 11/1994 | Bane | .................. | B65D 33/1691 206/459.5 |
| 5,606,846 A * | 3/1997 | Raby | .................. | B65D 33/1691 229/123.2 |
| 5,727,686 A * | 3/1998 | Kristal | .................... | B65D 33/34 156/581 |
| 5,824,380 A * | 10/1998 | Hagen | ....................... | B32B 3/04 428/41.9 |
| 6,428,867 B1 * | 8/2002 | Scott | ....................... | B32B 27/08 206/807 |
| 7,389,928 B2 * | 6/2008 | Lubow | .................. | G06K 17/00 235/462.01 |
| 7,815,123 B2 * | 10/2010 | Conner | ..................... | A61L 2/28 235/375 |
| 2004/0264813 A1 | 12/2004 | Steffens | | |
| 2005/0230961 A1 * | 10/2005 | Walley | .................. | G09F 3/0292 283/81 |
| 2013/0161938 A1 * | 6/2013 | Mayrhofer | ............ | G09F 3/0292 283/81 |
| 2015/0251829 A1 * | 9/2015 | Vogt | .................... | B65D 75/5838 206/459.1 |
| 2015/0255009 A1 * | 9/2015 | Akhter | .................. | G09F 3/0292 206/459.1 |
| 2015/0257632 A1 * | 9/2015 | Ramsey | ............. | A61B 1/00144 206/204 |
| 2016/0228676 A1 * | 8/2016 | Glithero | ............. | A61M 25/002 |
| 2017/0296282 A1 * | 10/2017 | Turturro | ................ | A61B 50/30 |
| 2018/0214232 A1 * | 8/2018 | Swinney | ................ | A61B 50/31 |

FOREIGN PATENT DOCUMENTS

| | | |
|---|---|---|
| GB | 1482523 | 8/1977 |
| GB | 2517774 A | 3/2015 |
| GB | 2526313 A | 11/2015 |
| WO | 9918001 A1 | 4/1999 |
| WO | 2003034936 A1 | 5/2003 |
| WO | 2005107823 A1 | 11/2005 |

\* cited by examiner

TRANSPORTATION OF MEDICAL INSTRUMENTS

FIELD OF THE INVENTION

The present invention relates to a device for the transportation and temporary storage of medical instruments such as endoscopes, laryngoscopes or other probes in a medical facility, and to a method of manufacturing the device.

BACKGROUND TO THE INVENTION

Various medical instruments are used for the internal examination of the human or animal body. Endoscopes, for example, are produced in a range of lengths and diameters depending on the intended use. Typically, an endoscope is flexible, and may have an internal channel, or lumen, down which fluids may be directed. Because of the invasive nature of endoscopy, it is necessary that an endoscope be thoroughly cleaned and disinfected after use on a patient before it is used for another procedure. After use, the endoscope undergoes a decontamination procedure involving cleaning, disinfecting and sterilising prior to re-use. WO 2005/107823 discloses a decontamination system which provides cleaning wipes to remove organic deposits, disinfectant/sterilising wipes and sterile rinse wipes to remove disinfectant residues. Each wipe is typically provided in its own sealed sachet which may provide information such as lot or batch number, date of manufacture and expiry date. This information may be transferred to a record book as part of an audit trail to provide a record that an instrument has been properly decontaminated and the date on which this was done.

Each sachet may also optionally be provided with a data carrier such as a bar code or RFID tag, and corresponding data carriers may be provided for the instrument to be decontaminated and for patient and operator details. When carrying out a decontamination procedure, each data carrier is read and a print-out may be produced which provides confirmation that the decontamination procedure has been carried out in accordance with correct procedure, and optionally details such as the instrument decontaminated, the operator, and data specific to a patient. These systems facilitate the provision of proper audit trails to ensure that an instrument is known to have been decontaminated in accordance with procedure.

Ideally, the decontamination procedure is carried out in close proximity to where the endoscope will be used, and preferably immediately before it is to be used. However, such ideal conditions seldom occur. Typically, a decontaminated instrument must be temporarily stored until required, and it may need to be used in a procedure room which is some distance from where decontamination took place.

For transportation of medical instruments such as endoscopes before and after use, it has been proposed in WO 2003/034936, to provide a re-usable tray having an endoscope compartment, a single-use disposable tray-liner having an open-faced pouch, and a pouch-closing protective cover. The tray-liner is impermeable to body fluids, and flexible enough that the pouch is able to conform to the contours of the endoscope compartment. When an endoscope is placed in the pouch within the endoscope compartment, the protective cover can be detachably extended across the open face of the pouch from one edge to another so as to enclose and protect the endoscope.

To provide traceability data, an operator may place a ticket carrying the data in the tray, under the tray-liner. A problem with this is that it is necessary to remove the protective cover and the tray-liner to access the traceability data. Movements in the course of this operation generate particles and increase the risk of contamination. An alternative, in which a ticket is placed on the instrument itself, also introduces an undesirable source of potential contamination.

Another transportation system provides two large instrument bags: one for decontaminated instruments and the other for contaminated instruments. The two bags may be of different colours to allow easy differentiation. However, the action of unfolding the bags is also liable to generate potentially contaminating particles.

SUMMARY OF THE INVENTION

According to the present invention there is provided a device as specified in the independent claims. Preferred features are specified in the dependent claims.

The invention provides an instrument bag that is easily sealed, ensuring no harmful organisms compromise the sterility of the decontaminated medical device. Contaminated instruments are kept in an enclosed environment, protecting healthcare staff from transmission of potentially harmful pathogens.

The invention provides visual evidence to a user when a sealed instrument bag has been opened so that the user knows that the bag is now suitable only for transportation of a dirty instrument to the decontamination room.

The invention also provides for traceability data to be transported along with the medical device, ensuring that patient and instrument records are always linked.

BRIEF DESCRIPTION OF THE DRAWINGS

The invention will now be further described, by way of example, with reference to the following drawings in which.

DETAILED DESCRIPTION

Figure 1:
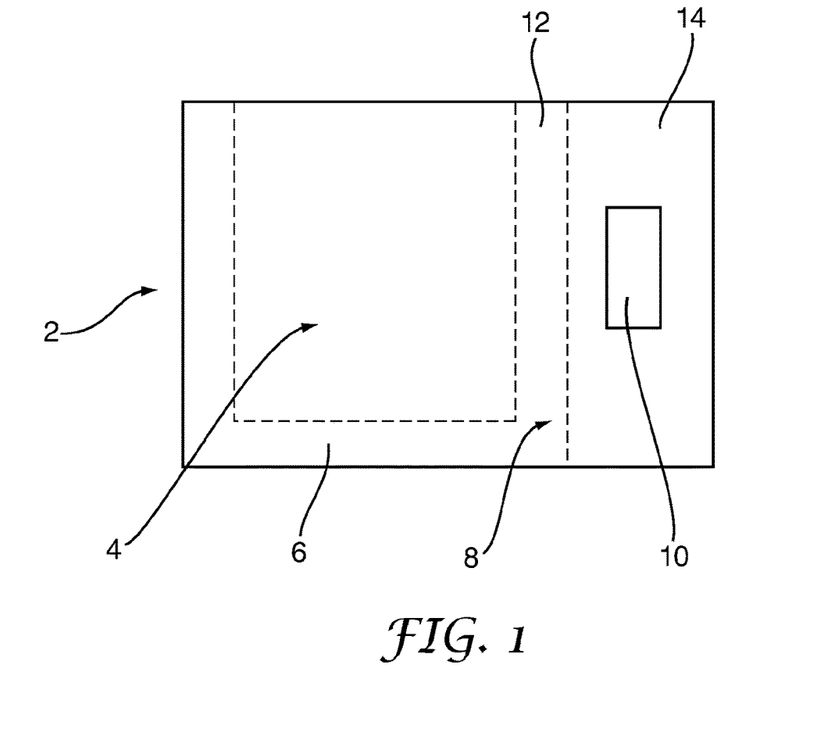
FIGS. 1 and 2 show stages in the manufacture of a label for use in an embodiment of the present invention.

The label 2 shown in FIG. 1 has a first portion 12 and a second portion 14 either side of a line 8 where a peelable backing is removable and protects an adhesive lower surface. A generally U-shaped peelable backing portion 6 is removable to define a pocket portion 4 when the first portion 12 is adhered to an instrument bag. The second portion 14 has an opening 10 which in this example is a window that is entirely surrounded by material of the second portion.

Figure 2:
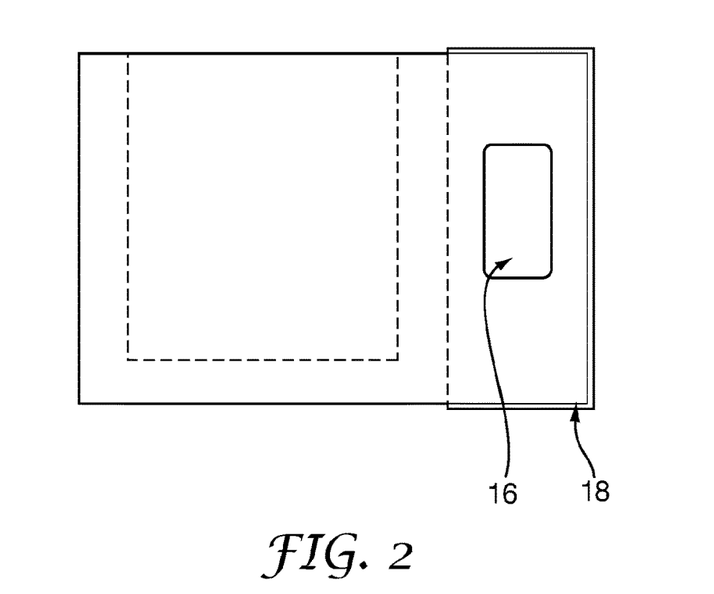

During manufacture, an adhesive-backed security seal or sticker 16 is laid over the opening 10 so that it is adhered around its outer edges, as shown in FIG. 2. A peelable backing 18 is provided on the lower surface of the second portion 14. This peelable backing covers the adhesive surface of the second portion 14 and also the exposed adhesive surface of the security seal 16. It will be appreciated that the peelable backing 18 could be provided as part of an original backing on the label 2, where the opening 10 is cut out and removed leaving the entire backing intact, or the peelable backing could be added or replaced after the security sticker 16 has been laid over the opening 10.

Figure 3:
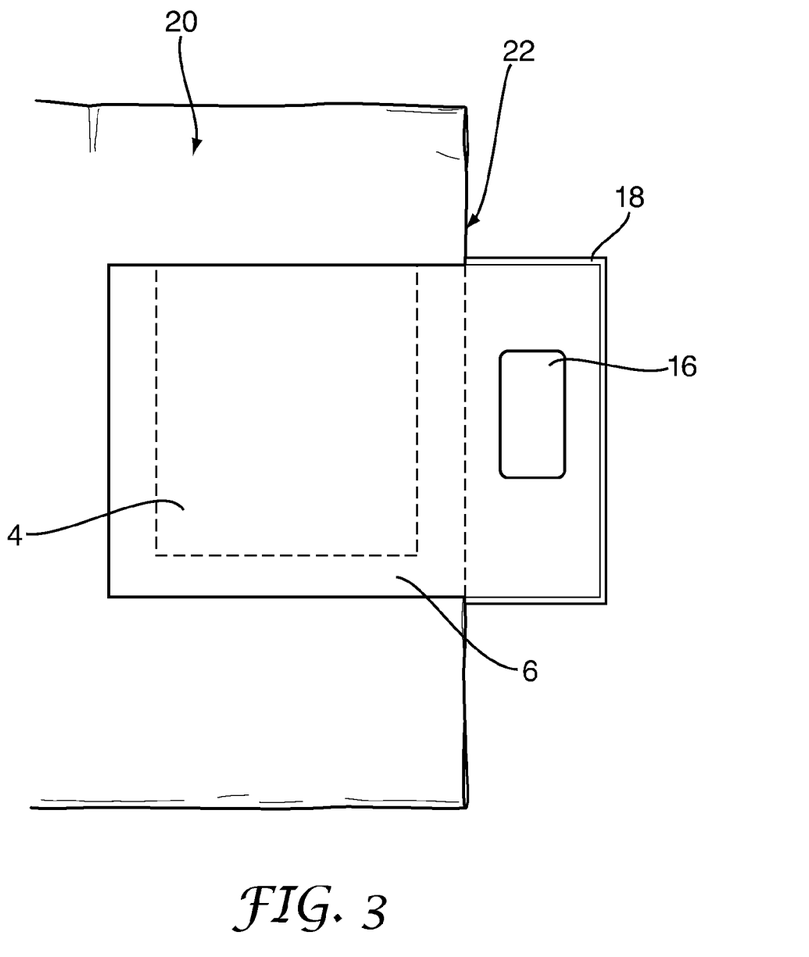
FIG. 3 illustrates a device in accordance with an embodiment of the invention.

Referring now to FIG. 3, an embodiment of the present invention is shown. Here, the U-shaped backing 6 has been removed during manufacture, and the exposed adhesive lower surface has been adhered to an instrument bag 20 which has an opening 22 for receiving an instrument. The bag 20 is formed from a plastics material which is impermeable to bodily fluids so that a user is protected from potentially harmful pathogens that may be present on a contaminated instrument sealed within the bag. The first portion 12 is adhered to an external portion of the bag 20 adjacent to the opening 22 where the generally U-shaped backing portion 6 has been removed. The second portion 14 is disposed beyond the opening 22 and has a lower surface at least a part of which is adhesive and covered by the removable backing 18. The device shown in FIG. 3 provides transportation and temporary storage for a medical instrument 24 such as a laryngoscope blade (FIGS. 4 and 5).

The instrument bags 20 may be sterilised by gamma-irradiation and provided in a suitable container (not shown). Each bag 20 may optionally be provided in its own outer bag formed of a fluid-impervious material and sealed to prevent ingress of contaminants.

When a decontaminated instrument 24 is to be transported to a theatre of use, the user removes one bag 20 from the container or outer bag and inserts the clean instrument 24 into the bag 20. The insertion may be facilitated by lifting the second portion 14 of the label to open up the opening 22 of the instrument bag with minimal contact.

Figure 4:
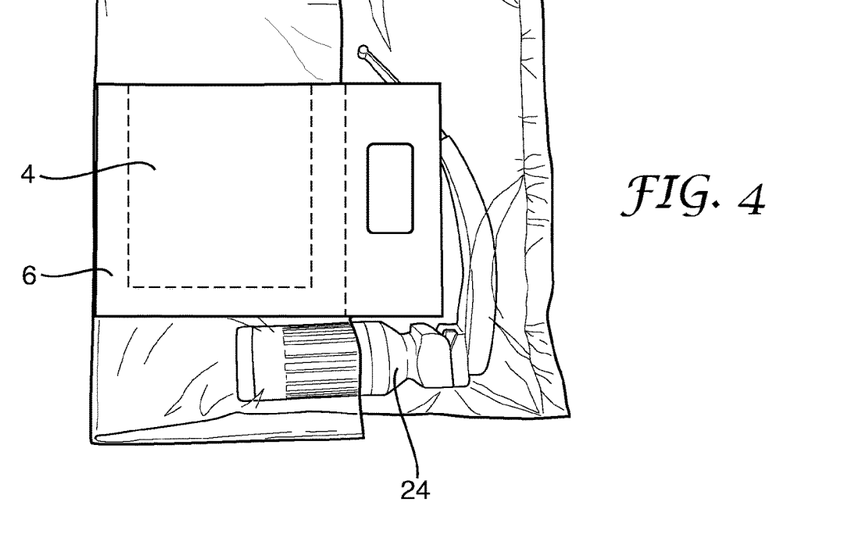
FIGS. 4 and 5 illustrate the device of FIG. 3 in use.
Figure 5:
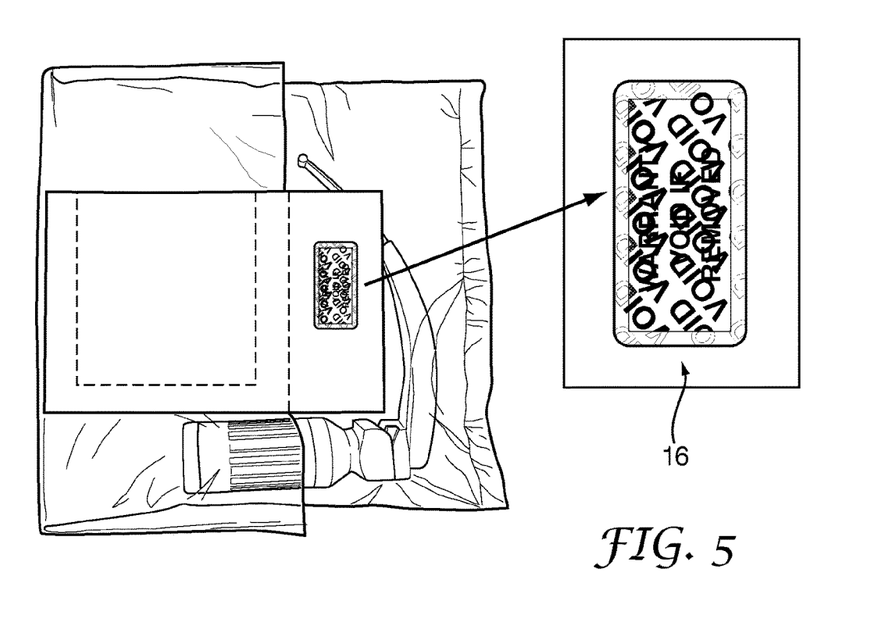

The user peels the backing 18 off the second portion 14 of the label 2, and seals the instrument bag 20 by pressing the exposed adhesive portion onto an outer surface of the instrument bag (FIG. 4). The entire lower surface of the second portion 14 in this embodiment is adhered to the outer surface of the bag, including the exposed lower surface of the tamper-evident seal portion 16. When first adhered to the surface of the bag 20, the tamper-evident portion 16 exhibits a first visual appearance. In this example, the appearance is blank but it will be appreciated that any suitable words or symbols could be used to denote an instrument bag which contains a clean instrument 24.

The user then places a data carrier (not shown) into the pocket 4. The data carrier may be a sachet of the sporicidal wipe used to disinfect the medical instrument 24 such as is described in WO 2005/107823; it will be understood that other data carriers may be used which will provide appropriate traceability information. Such information may include, but is not limited to, patient notes, instrument records, lot or batch number of the disinfectant used on the instrument, use-by date of the disinfectant. The instrument 24 is now ready for safe transport to the next patient, together with traceability data relating its disinfection.

When the instrument 24 is to be used, a medical professional sees from the first visual appearance that the instrument is clean and takes out the data carrier from the pocket 4. The instrument bag 20 is opened by peeling off the second portion 14 of the label 2. The clean seal is now broken. The clean instrument 24 is removed from the instrument bag 20 for use but the bag 20 is retained.

The peeling off of the second portion 14, including the tamper-evident portion 16, causes the tamper-evident portion to exhibit a second visual appearance which is different from the first visual appearance and which is evident even when the second portion 14 is subsequently adhered to the same surface of the bag 20.

After use, the contaminated instrument 24 is placed back in the instrument bag 20 (FIG. 5) and the user reseals the bag 20. The instrument 24 is now ready for safe transport to the decontamination room. The second visual appearance, which in this example shows multiple instances of the word VOID, warns the user and infection control that the bag 20 has been opened and that it is now only suitable to transport the dirty instrument back to the decontamination area. It will be understood that many other words or symbols may be used to provide the second visual appearance. Traceability data may again be stored in the pocket 4.

Various types of security seal or sticker 16 are known per se to those skilled in the art of security label making. Suitable tamper-evident labels or seals are commercially available and may be used in the present invention; for example, by Shenzen Fullgo Security Packaging Technology Co., Ltd. An example is shown at: www.sticker-tapes.com/Non-Transfer-Warranty-Void-Security-Sticker-1.

Figure 6:
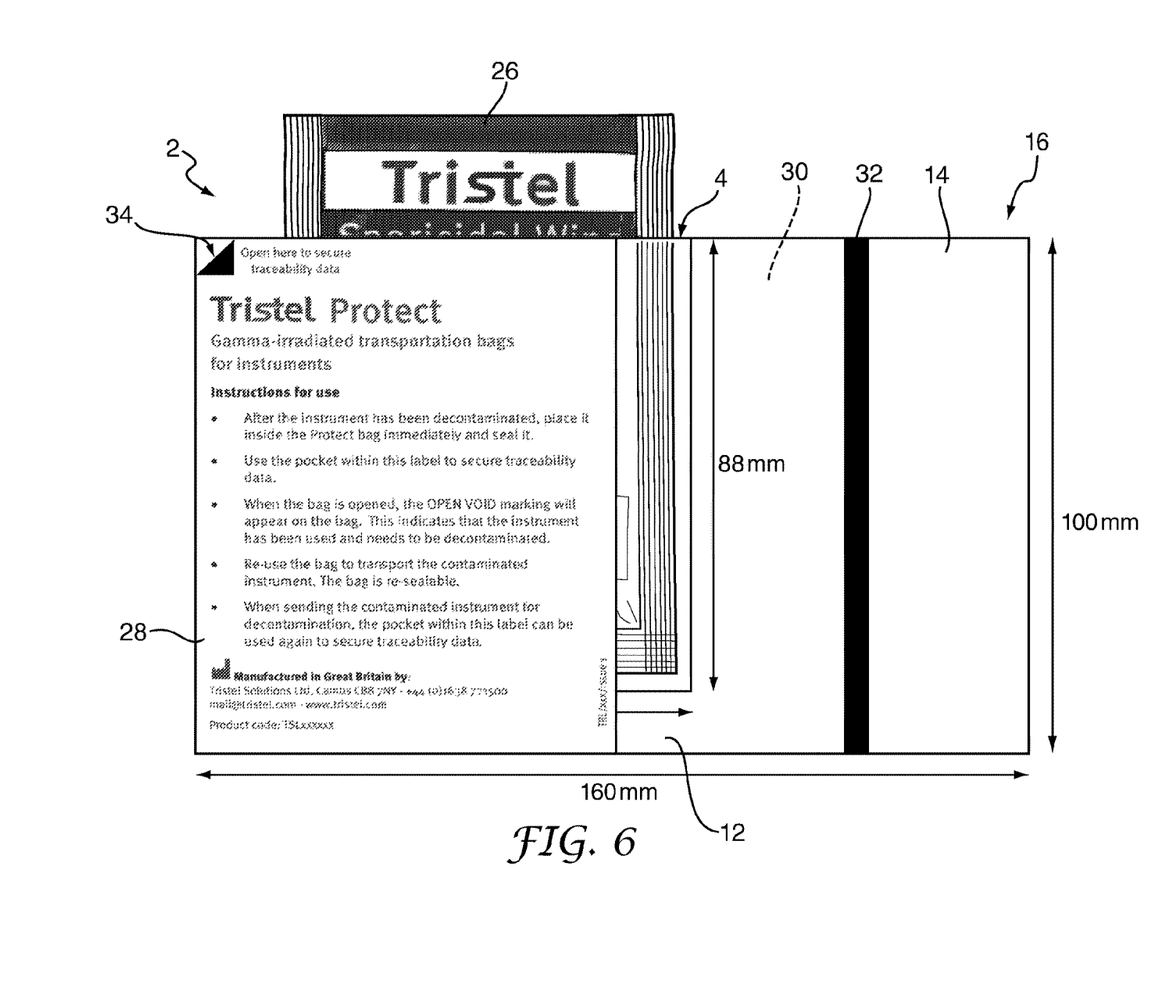
FIGS. 6 and 7 show a label for use in an alternative embodiment of the present invention.

Referring now to FIG. 6, another embodiment of label 2 for use in the invention comprises an upper layer 28 and a lower layer 30. The lower layer 30 is coloured and contains the tamper-evident seal portion 16. Non-limiting dimensions are given for illustrative purposes. In this example, the upper layer 28 has the same dimensions as the lower layer and is adhered to the lower layer except in an area defining a pocket 4 for a data carrier 26. In this example, the data carrier 26 is a sporidical wipe sachet. The left side of the upper layer 28 is white in this embodiment, and the right side is transparent or translucent to allow viewing of the tamper-evident seal portion 16 and part of the pocket 4. The pocket 4 may be formed by providing the upper layer 28 with a suitably-shaped peelable backing portion, removal of which permits the upper layer 28 to be adhered to the lower layer 30 around an area which is shaped to receive a data carrier 26.

A 'hinge' portion 32 defines a location to the right of which a user will remove the peelable backing to seal an instrument bag to which the label 2 is adhered. The left side of the lower layer 30 has a peelable backing, which is peeled off during the production process to adhere the label to an instrument bag with the right side disposed beyond the opening of the instrument bag. After an instrument has been decontaminated, the user places it in the instrument bag and seals it by removing the peelable backing from the tamper-evident seal portion 16 of the lower layer 30 and pressing the exposed adhesive layer against an outer surface of the instrument bag.

The user uses the pocket 4 to secure the data carrier 26 between the upper and lower layers. This may conveniently be done by the user peeling the left side of the upper layer 28 from the lower layer 30 far enough to expose the pocket area 4, breaking the upper layer 28 at a pre-formed peel line 34. The user then lays the data carrier 26 in the pocket area and re-seals the left side of the upper layer 28. When the instrument bag has been opened by unsealing the tamper-evident seal portion 16, this portion exhibits a second visual appearance which in this example includes the words OPEN VOID (FIG. 7) on the label 16 and on a transfer layer 38 on the bag. This indicates that the instrument has been used and needs to be decontaminated before further use. The used instrument may be replaced in the instrument bag and transported to a decontamination facility, either directly or via a storage facility. During the return trip, the pocket 4 may again be used for storing traceability information on a data carrier.

Figure 8:
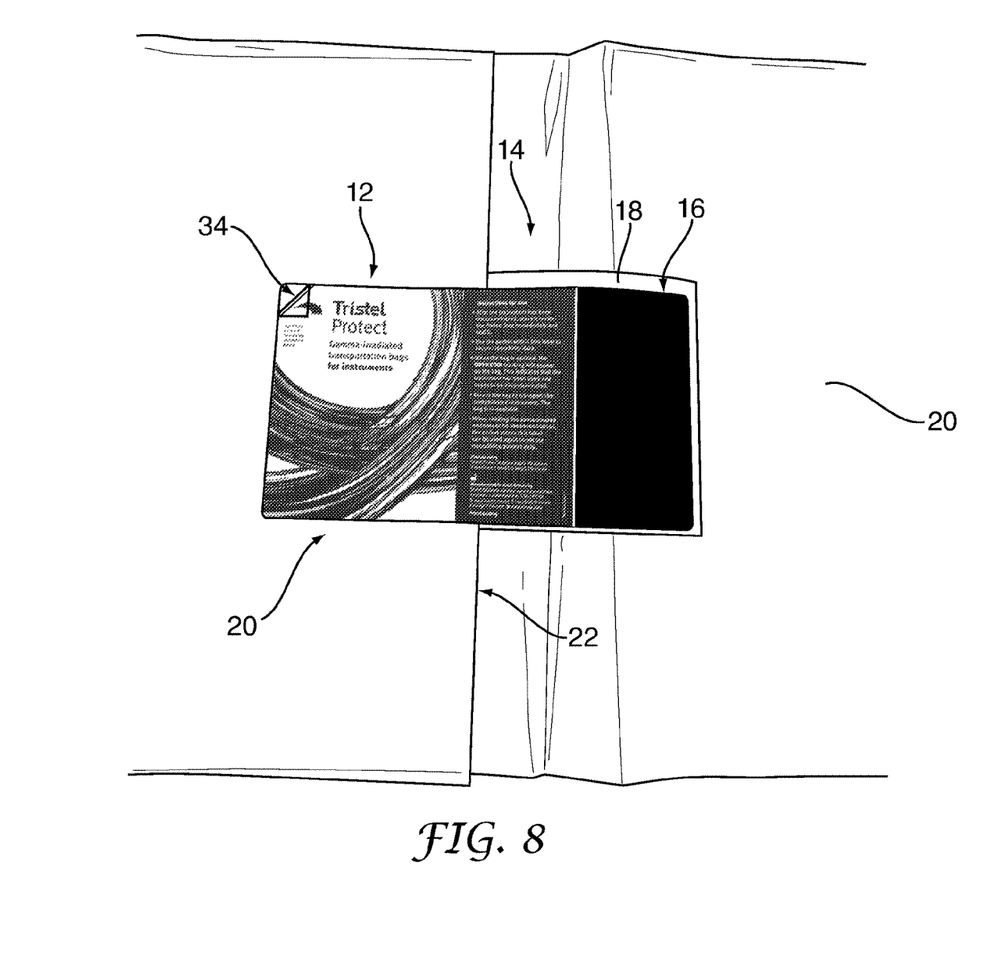
FIGS. 8 to 13 show a label and its use in a further embodiment of the invention.

Referring now to FIG. 8, a further embodiment of the label 2 is of similar construction to the label of FIG. 6, having an upper layer releasably adhered to a lower layer which includes tamper-evident seal portion. Here, the first portion 12 is opaque and carries instructions for use. The second portion 14 is disposed beyond the opening 22 of an instrument bag 20 when the first portion 12 is adhered to the bag.

To initially seal the bag 20, the user removes the peelable backing 18 from the second portion 14 of the label and presses the second portion 14 onto a surface of the bag adjacent the bag opening 22.

Figure 9:
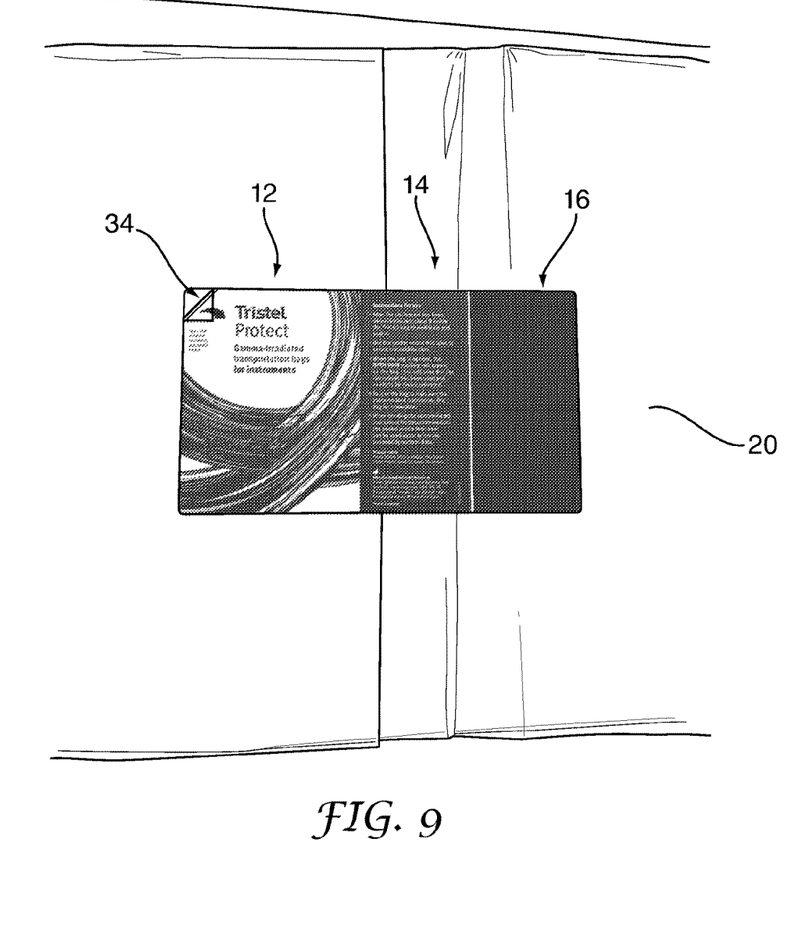

Once the tamper-evident seal portion 16 has been first adhered to a surface of the bag (FIG. 9) it exhibits a first visual appearance. In this example, the first visual appearance is a uniform blue colour which is the same as the appearance of the tamper-evident seal portion 16 when on the label with peelable backing 18 (FIG. 8).

Figure 10:
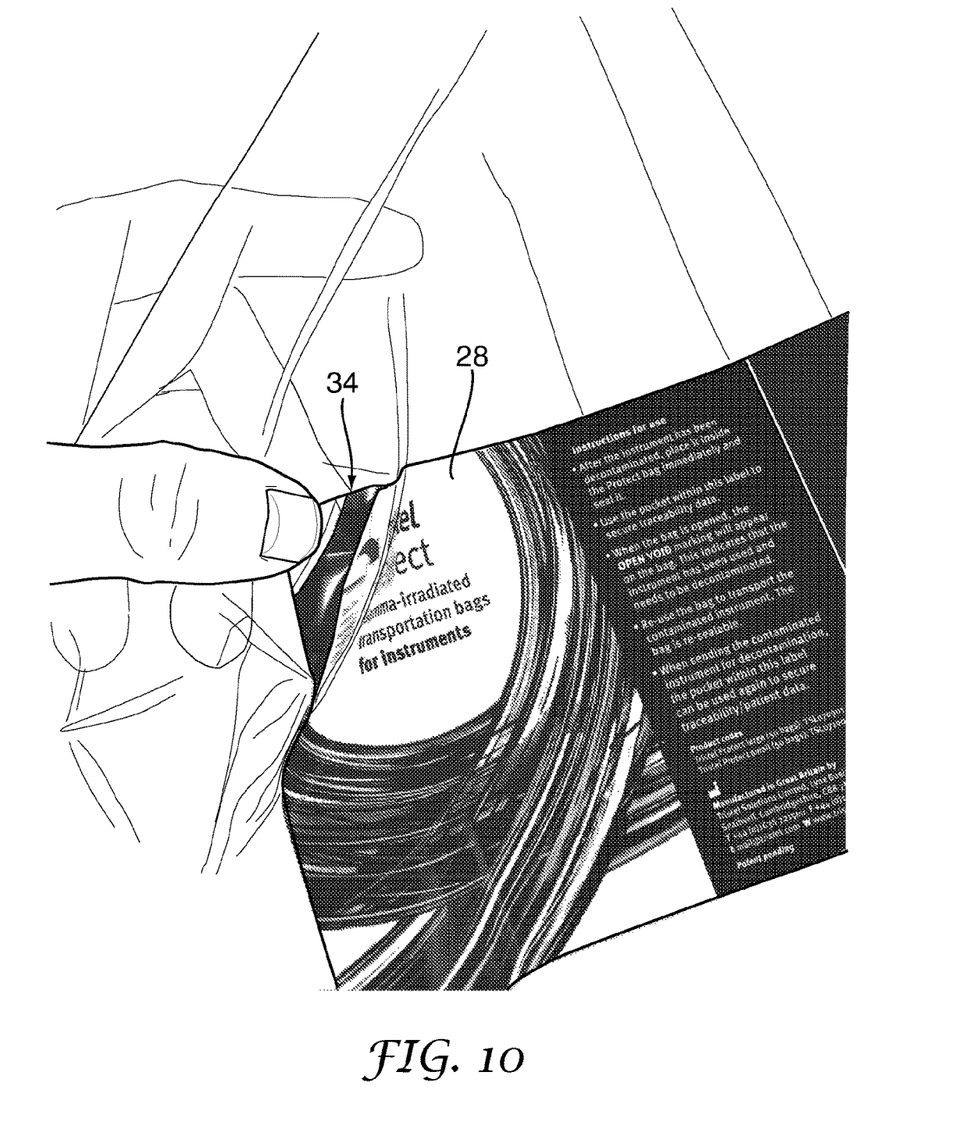
Figure 11:
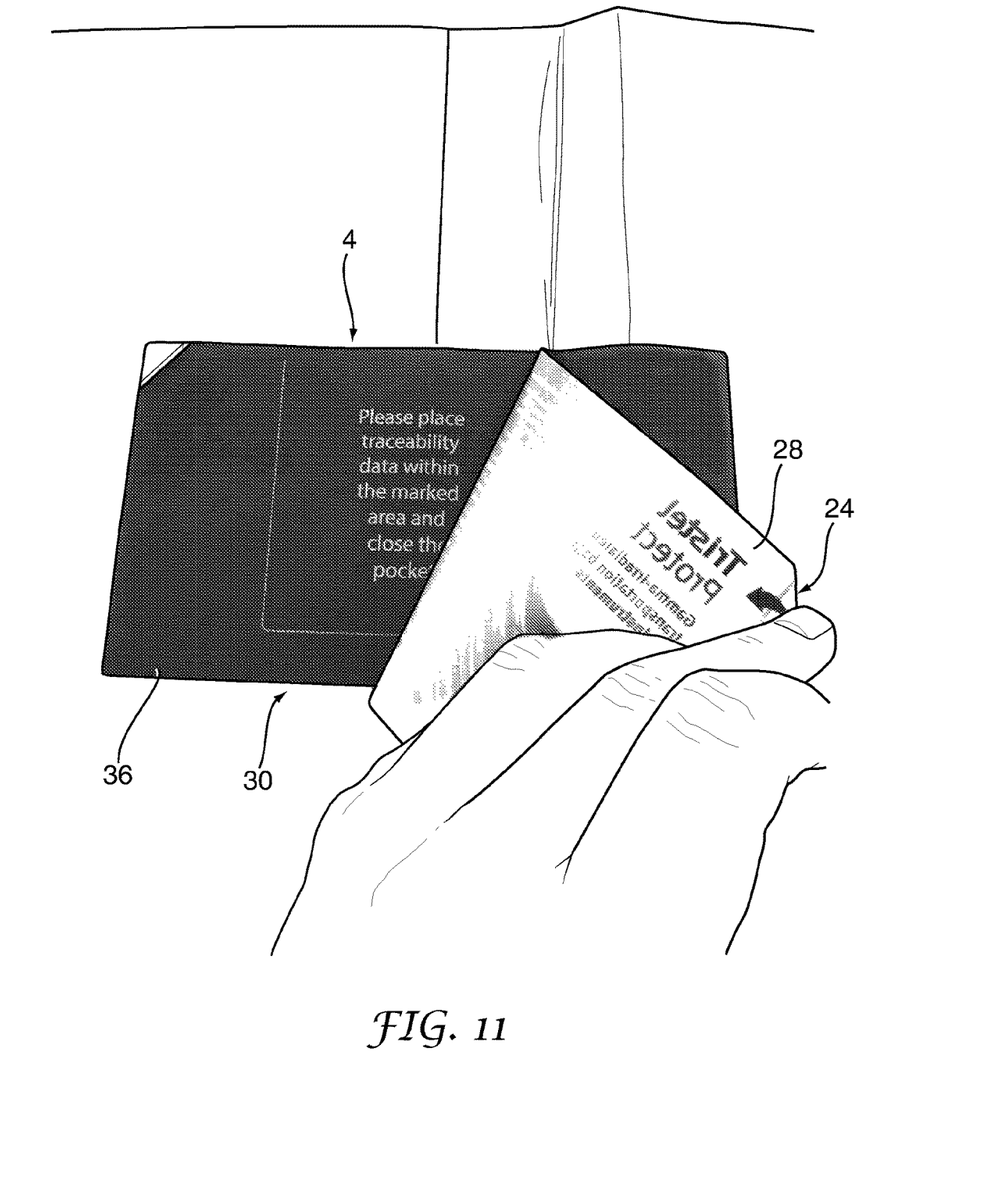
Figure 12:
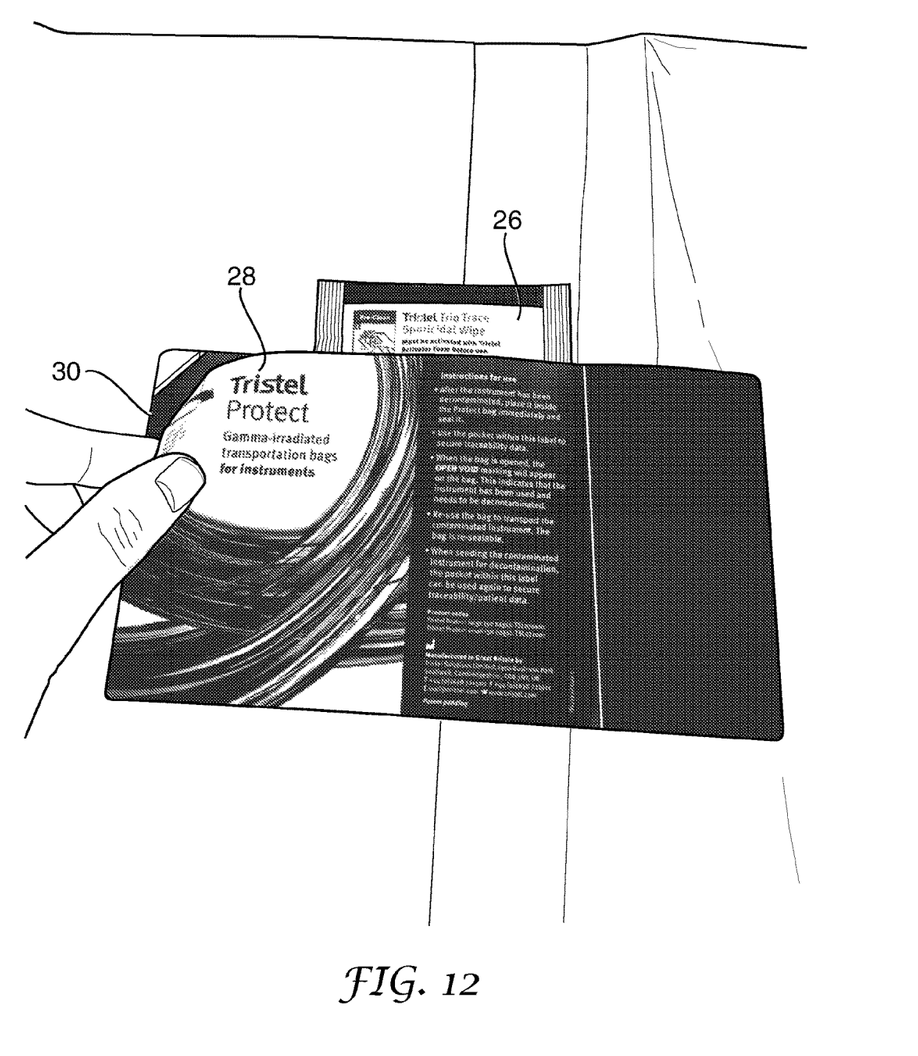

To access the pocket 4 the user presses a corner of the label by the peel line 34 (FIG. 10) to release the upper layer 28 at the peel line 34. The user then peels the top layer 28 away from the lower layer 30 of the label (FIGS. 11 & 12). A sachet or data carrier 26 is placed in the pocket area 4 and the upper layer 28 is resealed over the lower layer 30. The lower surface of the upper layer 28 is provided with a releasable adhesive coating in the area which covers the area 36 around the pocket 4 but not in the area of the pocket. After resealing of the upper layer 28, the data carrier is securely held in the pocket 4, along with any instrument in the bag, until it is removed by again peeling away the upper layer 28.

Figure 7:
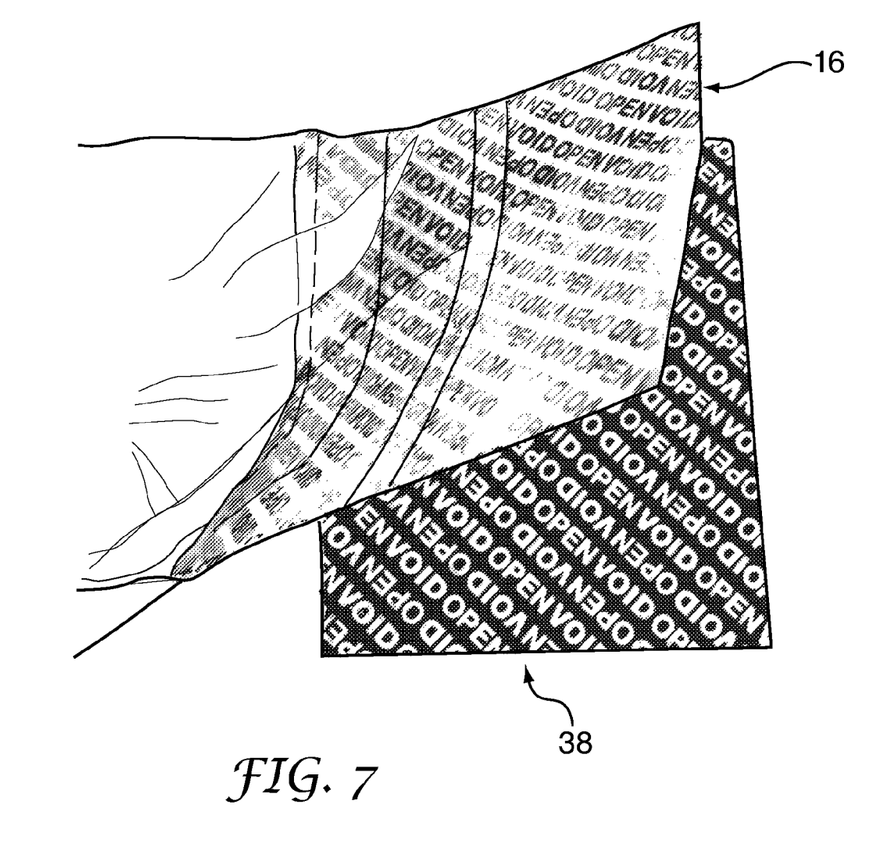
Figure 13:
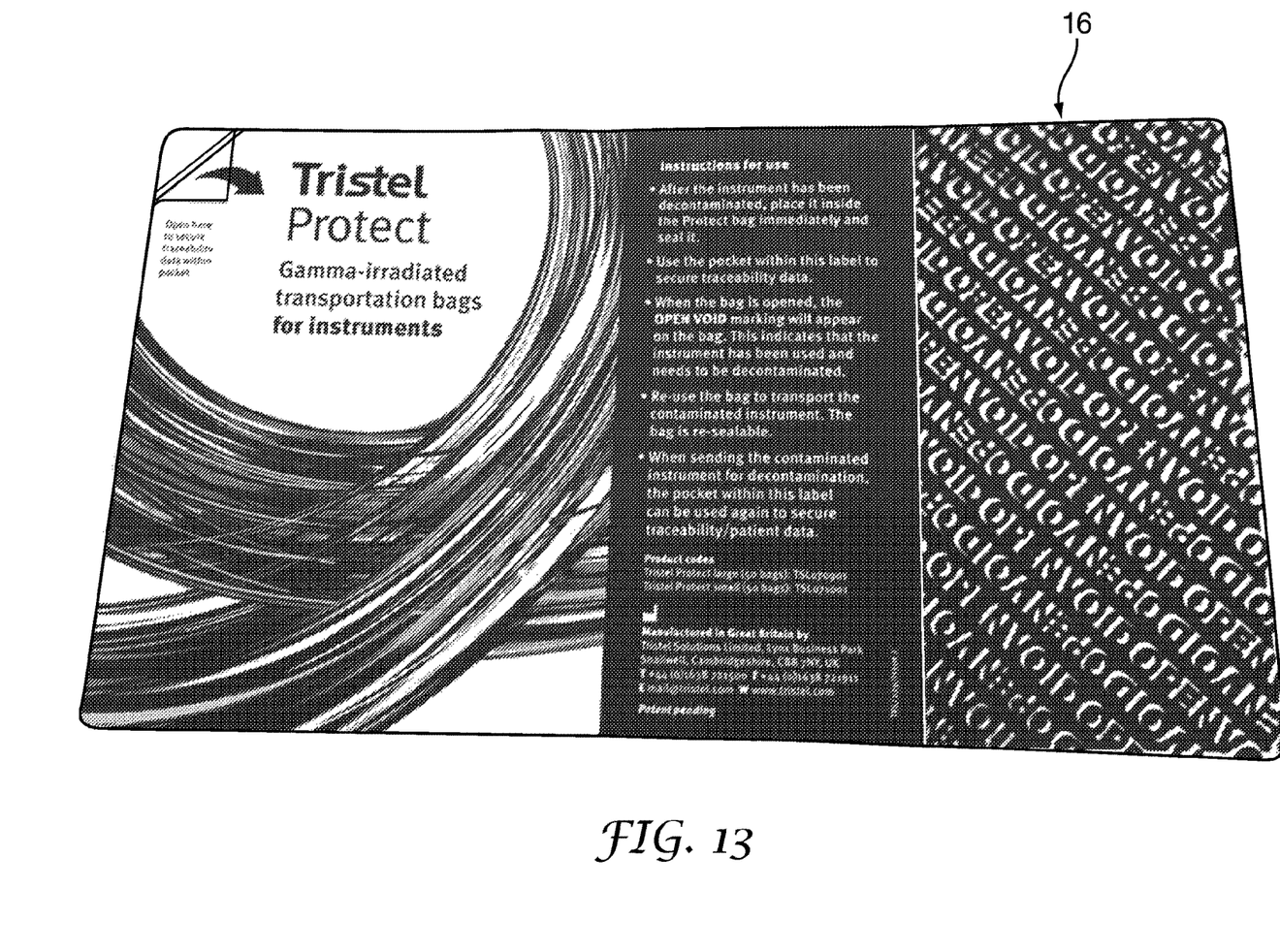

The tamper-evident seal portion 16 exhibits a second visual appearance after it has been adhered to and then removed from a surface of the bag, and subsequently adhered to the same surface of the bag. The second visual appearance (FIG. 13) is different from the first visual appearance. Even replacing the seal portion 16 in the exact location where it was originally placed on the bag produces a second visual appearance which is different from the first visual appearance and provides a clear indication that the seal has been broken. In this example, the tamper-evident seal portion 16 includes a transfer layer 38 (as illustrated in FIG. 7) part of which preferentially adheres to the surface of the bag rather than the lower surface of the upper layer 28. The transfer is therefore 'permanent' in the sense that the transfer layer 38 does not subsequently re-adhere to the upper layer 28, and the tamper-evident portion 16 never regains its first visual appearance.

In this example, the lower layer 30 of the label 2 is made from 50 µm polypropylene, with a permanent acrylic-based adhesive (Adhesive 62D, from Herma GmbH), approx. 18 µm calibre. The peelable backing 18 is a 70 µm two-sided release (2:1) bleached supercalendered kraft utilizing a silicone material for smooth release from the tamper-evident transfer layer 38. The upper layer 28 is PP 50 transparent tc (885) (Herma GmbH) a 50 µm transparent, glossy, biaxially oriented polypropylene film with topcoat to facilitate printing. The materials used in this example are for illustrative purposes only and do not limit the invention. It will be appreciated that many other materials and combinations of materials may be used in the present invention and will be known to persons skilled in the art of security label making.

It will be appreciated that various sizes of instrument bag may be used depending on the size of the instruments they are to contain.

The upper surface of the label may be blank apart from the tamper-evident portion, or it may optionally contain technical or marketing information, or any other desired words, colours or symbols.

The terms "upper" and "lower" and the like are relative and to be construed having regard to the context of the described embodiments.

The articles "a" and "an" are used herein to mean "at least one" where the context permits.

The invention claimed is:

1. A device for the transportation and temporary storage of a medical instrument, the device comprising:
   an instrument bag formed of a plastics material substantially impermeable to bodily fluids, the bag having a bag opening for receiving the instrument; and
   a label which has a first portion adhered to an external surface of the bag adjacent to the bag opening and has a second portion which is disposed beyond the bag opening and which has a lower surface at least part of which is adhesive and covered by a removable backing; wherein:
   the first portion of the label includes a pocket for receiving a sachet or data carrier;
   the second portion of the label includes a tamper-evident portion which exhibits a first visual appearance when first adhered to a surface of the bag, and which exhibits a second visual appearance after it has been adhered to and then removed from a surface of the bag, and subsequently adhered to the same surface of the bag; and wherein the second visual appearance is different from the first visual appearance.

2. The device according to claim 1, wherein the second portion of the label has a second portion opening and wherein the tamper-evident portion comprises a tamper-evident sticker which overlies the second portion opening.

3. The device according to claim 2, wherein the second portion opening is entirely surrounded by material of the second portion of the label.

4. The device according to claim 1, wherein the label comprises a bottom layer and a top layer, the tamper-evident portion being part of the bottom layer; the top layer having a lower surface releasably adhered to the bottom layer.

5. The device according to claim 1, wherein the pocket is defined by a first region of the lower surface of the label which is not adhered to the surface of the bag.

6. The device according to claim 1, wherein a lower surface of the first portion of the label has an adhesive portion which is generally U-shaped.

7. The device according to claim 4, wherein the first portion of the label includes the pocket for receiving a sachet or data carrier, the pocket defined by a region of the lower surface of the top layer which is not adhered to the bottom layer.

8. The device according to claim 1, wherein the pocket extends to an edge of the label.

9. The device according to claim 1, wherein the first visual appearance includes information denoting that the contents of the bag are clean.

10. The device according to claim 1, wherein the second visual appearance includes information denoting that the contents of the bag are contaminated.

11. The device according to claim 1, wherein the tamper-evident portion of the label includes a transfer layer, at least part of which becomes permanently adhered to a surface of the bag when the tamper-evident portion is first adhered to the bag.

12. A method of manufacturing a device as specified in claim 1, comprising:

providing an instrument bag formed of a plastics material substantially impermeable to bodily fluids, the bag having a bag opening for receiving a medical instrument;

providing a label which has a first portion and a second portion, the second portion having a lower surface at least part of which is adhesive and covered by a removable backing; wherein:

the first portion of the label includes a pocket for receiving a sachet or data carrier;

the second portion of the label includes a tamper-evident portion which exhibits a first visual appearance when first adhered to a surface of the bag, and which exhibits a second visual appearance after it has been adhered to and then removed from a surface of the bag, and subsequently adhered to the same surface of the bag; the second visual appearance different from the first visual appearance; and adhering the first portion to an external surface of the bag adjacent to the opening so that the second portion is disposed beyond the bag opening.

13. The method according to claim 12, wherein the first portion of the label has an adhesive lower surface covered by a removable backing; the step of adhering the first portion to an external surface of the bag including the step of removing at least part of said removable backing.

14. The method according to claim 13, wherein said at least part of said removable backing comprises a generally U-shaped portion whereby the pocket is defined by a first region of the lower surface of the label which is not adhered to the surface of the bag and which extends to an edge of the label.

15. The method according to claim 12, wherein the label comprises a bottom layer and a top layer, the tamper-evident portion being part of the bottom layer; the top layer having a lower surface releasably adhered to the bottom layer.

* * * * *